(12) United States Patent
Wheeler et al.

(10) Patent No.: US 10,953,408 B2
(45) Date of Patent: Mar. 23, 2021

(54) PATTERNED OPTOELECTRONIC TWEEZERS

(71) Applicant: The Governing Council of the University of Toronto, Toronto (CA)

(72) Inventors: Aaron Wheeler, Toronto (CA); Shuailong Zhang, Toronto (CA)

(73) Assignee: THE GOVERNING COUNCIL OF THE UNIVERSITY OF TORONTO BANTING INSTITUTE, Toronto (CA)

( * ) Notice: Subject to any disclaimer, the term of this patent is extended or adjusted under 35 U.S.C. 154(b) by 0 days.

(21) Appl. No.: 16/560,549

(22) Filed: Sep. 4, 2019

(65) Prior Publication Data

US 2020/0094264 A1 Mar. 26, 2020

Related U.S. Application Data

(60) Provisional application No. 62/726,657, filed on Sep. 4, 2018.

(51) Int. Cl.
*B03C 5/00* (2006.01)
*G01N 15/10* (2006.01)
*B01L 3/00* (2006.01)
*B03C 5/02* (2006.01)

(52) U.S. Cl.
CPC .............. *B03C 5/005* (2013.01); *B01L 3/508* (2013.01); *B03C 5/026* (2013.01); *G01N 15/10* (2013.01); *B01L 2200/0668* (2013.01); *B01L 2300/12* (2013.01)

(58) Field of Classification Search
CPC ......... B03C 5/005; B03C 5/025; B60L 3/508; B60L 2200/0668; B60L 2300/12; B60L 3/502761; G01N 15/10
See application file for complete search history.

(56) References Cited

U.S. PATENT DOCUMENTS

| | | | |
|---|---|---|---|
| 7,956,339 B2 * | 6/2011 | Ohta | B82Y 20/00 250/559.04 |
| 9,144,806 B2 * | 9/2015 | Chen | B03C 5/005 |
| 2007/0242719 A1 * | 10/2007 | Spoonhower | H01S 5/36 372/50.124 |

(Continued)

OTHER PUBLICATIONS

S. L. Neale, et al. "Trap profiles of projector based optoelectronic tweezers (OET) with HeLa cells", Opt. Express. 2009, 17 (7), 5231.

(Continued)

*Primary Examiner* — David E Smith
(74) *Attorney, Agent, or Firm* — Myers Bigel, P.A

(57) ABSTRACT

A patterned optoelectronic tweezers (p-OET) device is provided. The p-OET device includes a top and a bottom electrode arranged in a parallel spaced apart relationship. A patterned photoconductor layer is provided on the bottom electrode, and forms a pattern comprising at least one raised region where the bottom electrode is coated by a photoconductor material and at least one hollow region where the bottom electrode is exposed. The pattern includes one or more boundaries between the raised and hollow regions. In some implementations, the boundaries of the patterned photoconductive layer define a permanent trap feature.

24 Claims, 11 Drawing Sheets
(2 of 11 Drawing Sheet(s) Filed in Color)

(56) References Cited

U.S. PATENT DOCUMENTS

| | | | |
|---|---|---|---|
| 2009/0170186 A1* | 7/2009 | Wu | B01L 3/502761 435/286.1 |
| 2014/0116881 A1* | 5/2014 | Chapman | G01N 27/44791 204/451 |
| 2017/0226453 A1* | 8/2017 | Yang | B01L 3/502707 |

OTHER PUBLICATIONS

S. L. Neale, et al. "The resolution of optical traps created by Light Induced Dielectrophoresis (LIDEP)", Opt. Exp. 2007, 15, 12619.

S. B. Huang, et al. "High-purity and label-free isolation of circulating tumor cells (CTCs) in a microfluidic platform by using optically-induced-dielectrophoretic (ODEP) force" Lab Chip, 2013, 13, 1371.

S. Zhang, et al. "Manipulating and assembling metallic beads with Optoelectronic Tweezers", Sci. Rep., 2016, 6, 32840.

S. Xie, et al. "Programmable micrometer-sized motor array based on live cells", Lab Chip, 2017, 17, 2046.

R. Pethig, "Review Article—Dielectrophoresis: Status of the theory, technology, and applications", Biomicrofluidics, 2010, 4, 022811.

P. Y. Chiou, et al. "Massively parallel manipulation of single cells and microparticles using optical images", Nature, 2005, 436, 370.

M. C. Wu, "Optoelectronic Tweezers", Nat. Photon., 2011, 5, 322.

W. Choi, et al. "Programmable manipulation of motile cells in optoelectronic tweezers using a grayscale image", Appl. Phys. Lett., 2008, 93, 143901.

M. Z. Hoeb, et al. "Light-induced dielectrophoretic manipulation of DNA", Biophys. J., 2007, 93, 1032.

Y. H. Lin, et al. "Manipulation of single DNA molecules by using optically projected images", Opt. Exp., 2009, 17,15318.

A. T. Ohta, et al. "Motile and non-motile sperm diagnostic manipulation using optoelectronic tweezers",Lab Chip, 2010, 10, 3213.

S. M. Yang, et al. "Dynamic manipulation and patterning of microparticles and cells by using TiOPc-based optoelectronic dielectrophoresis", Opt. Lett., 2010, 35, 1959.

H. Hwang, et al. "Optoelectrofluidic platforms for chemistry and biology", Lab Chip, 2011, 11, 33.

L. Y. Ke, et al. "Cancer immunotherapy µ-environment LabChip: taking advantage of optoelectronic tweezers", Lab Chip, 2018, 18, 106.

M. Woerdemann, et al. "Advanced optical trapping by complex beam shaping", Las. & Photon. Rev., 2013, 7,839.

A. Jamshidi, et al. "Dynamic manipulation and separation of individual semiconducting and metallic nanowires", Nat. Photon., 2008, 2, 86.

P. J. Pauzauskie, et al. "Parallel trapping of multiwalled carbon nanotubes with optoelectronic tweezers", Appl. Phys. Lett., 2009, 95, 113104.

A. Jamshidi, et al. "NanoPen: dynamic, low-power, and light-actuated patterning of nanoparticles", Nano Lett. 2009, 9, 2921.

H. Y. Hsu, et al. "Phototransistor-based optoelectronic tweezers for dynamic cell manipulation in cell culture media", Lab Chip, 2010, 10, 165.

S. M. Yang, et al. "Cell patterning via diffraction-induced optoelectronic dielectrophoresis force on an organic photoconductive chip", Lab Chip, 2013, 13, 3893.

S. L. Neale, et al. "Trap Stiffness in Negative Optoelectronic Tweezers (OET)",presented at Conference on Lasers and Electro-Optics (p. CThLL6), San Jose, California, United States, May 2008.

A. T. Ohta, et al. "Dynamic cell and microparticle control via optoelectronic tweezers", J. Microelectromech., Syst. 2007, 16, 491.

S. Zhang, et al. "Escape from an Optoelectronic Tweezer Trap: experimental results and simulations", Opt. Exp., 2018, 26, 5300.

Zhang, et al. "Use of optoelectronic tweezers in manufacturing—accurate solder bead positioning", Appl. Phys. Lett., 2016, 109, 021110.

* cited by examiner

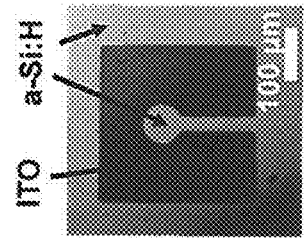
FIG. 3A
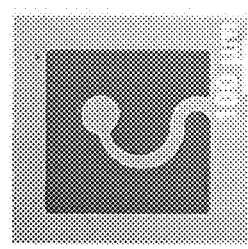
FIG. 3B
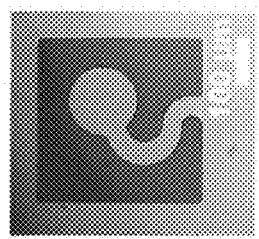
FIG. 3C
FIG. 3D
FIG. 3E

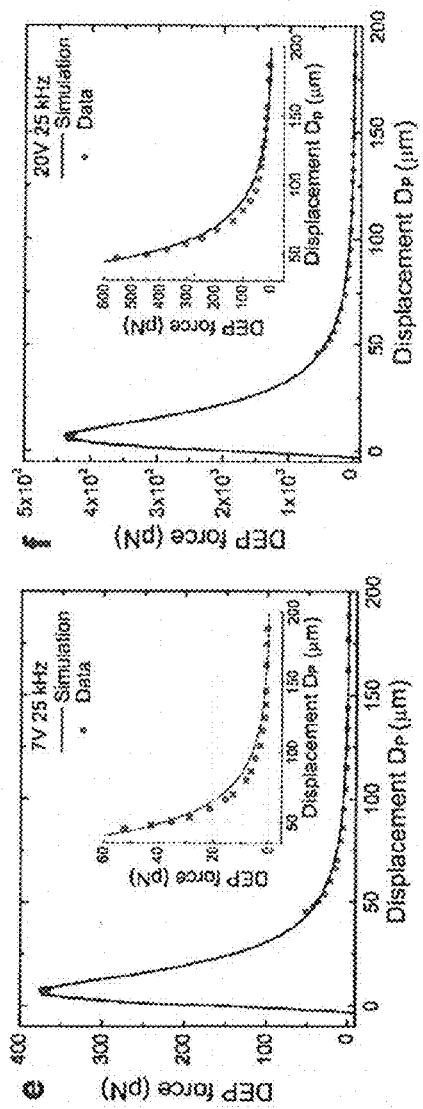
FIG. 5A  FIG. 5B
FIG. 5C  FIG. 5D
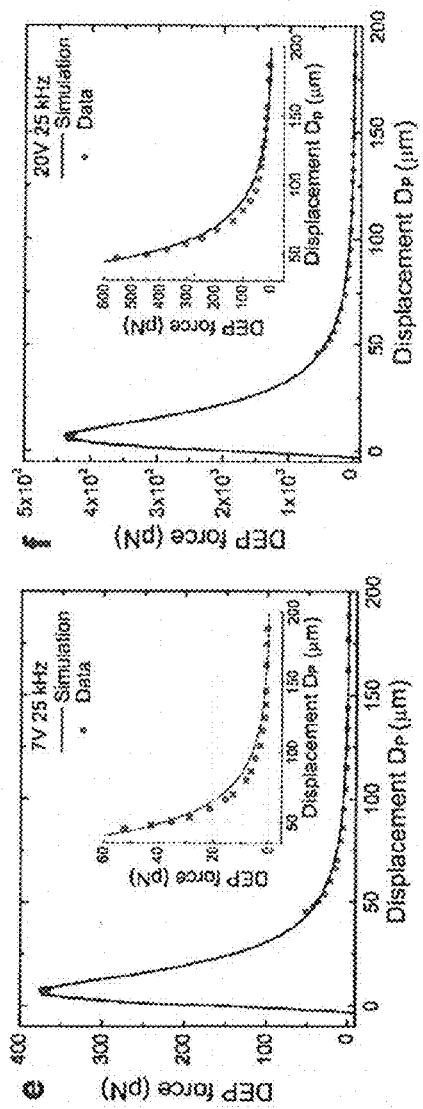
FIG. 5E
FIG. 5F
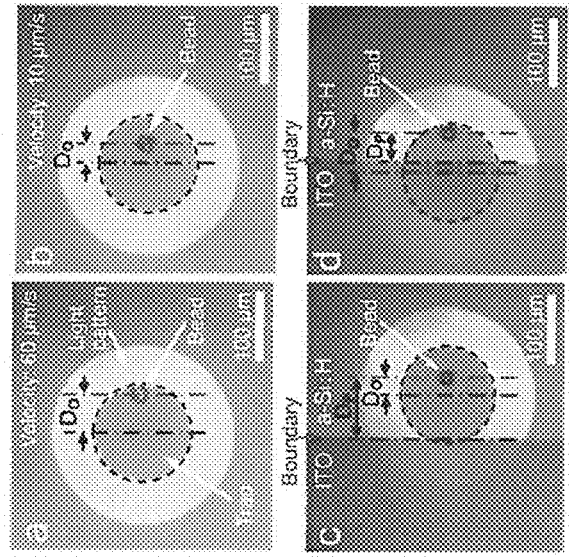
FIG. 5G
FIG. 5H
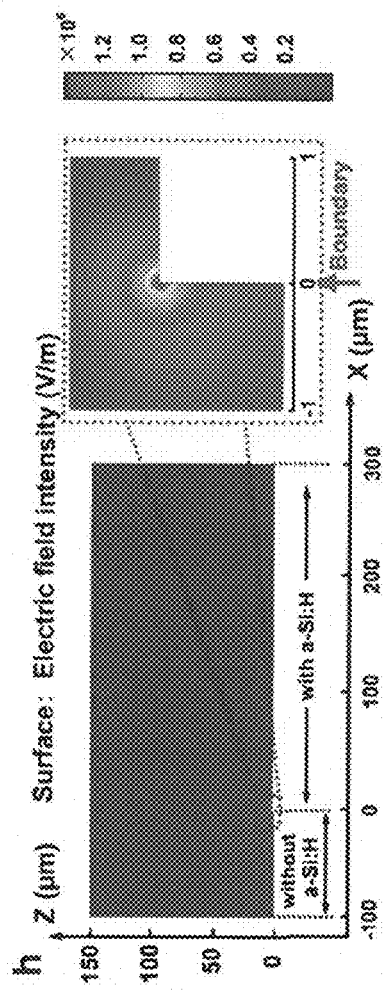

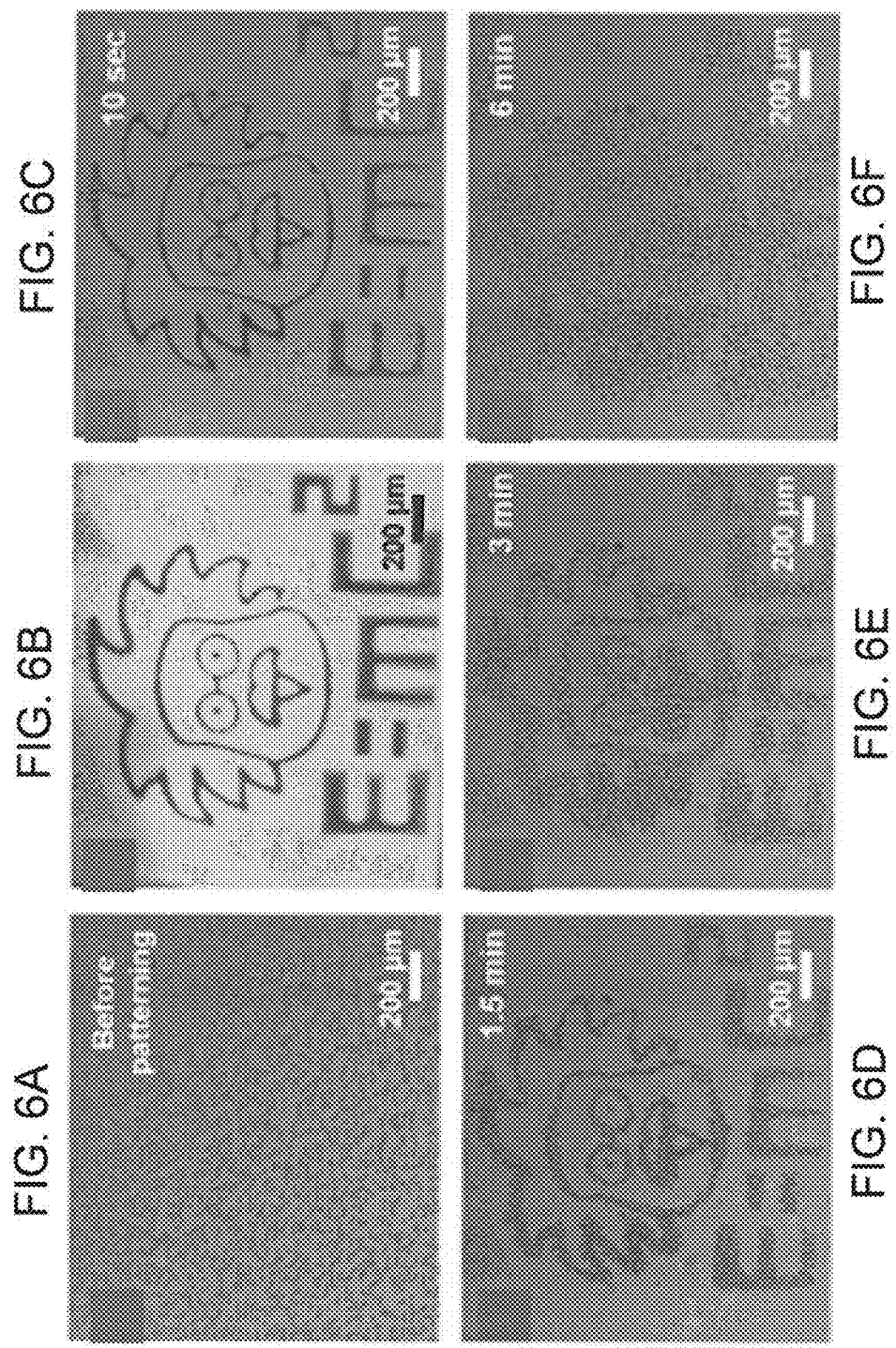

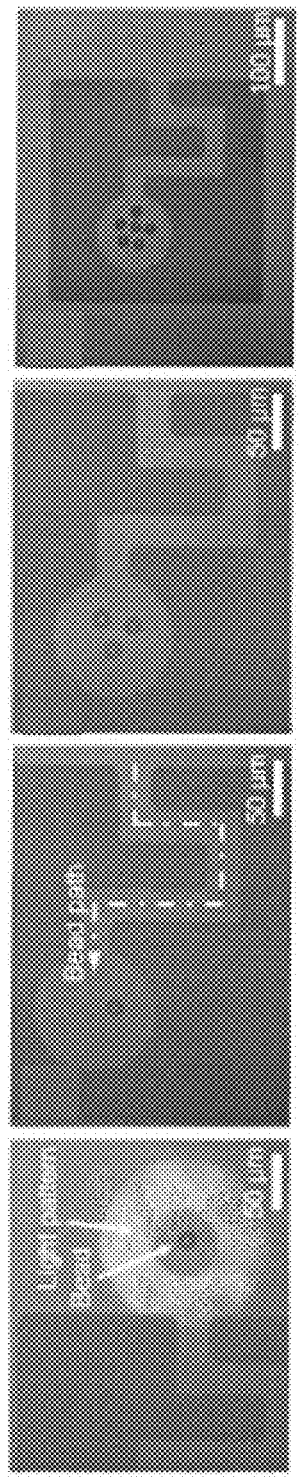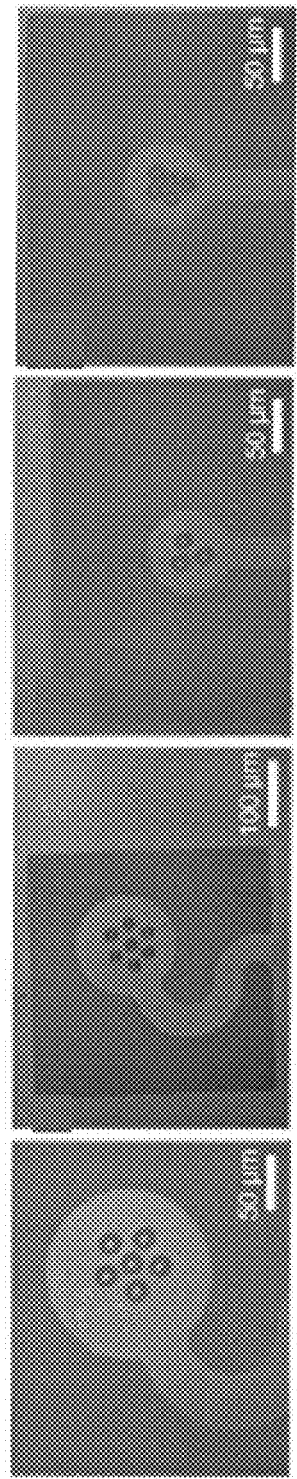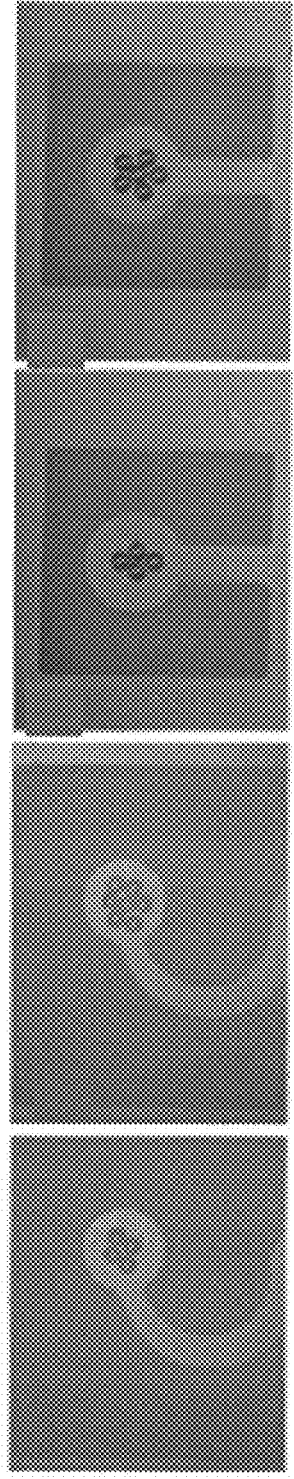

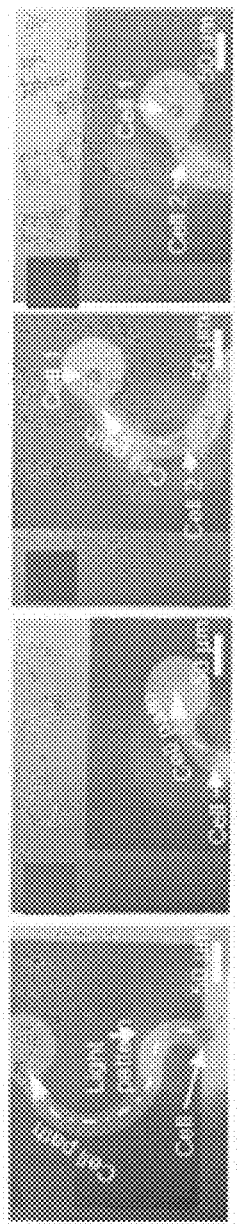
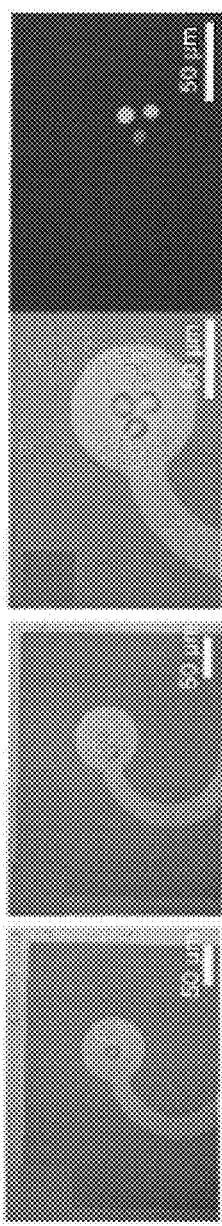
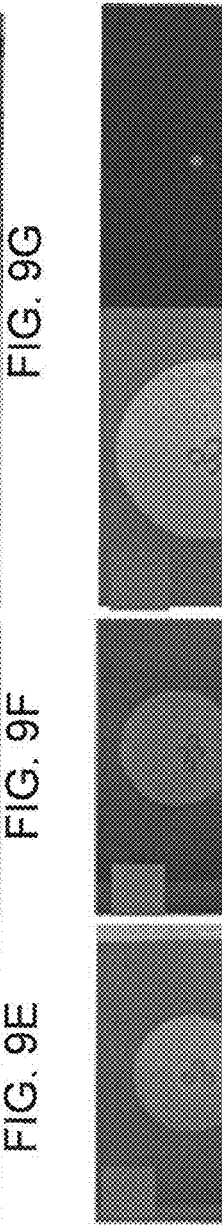
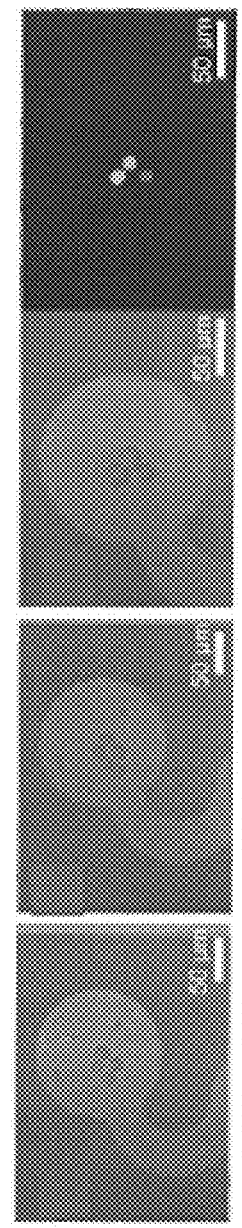

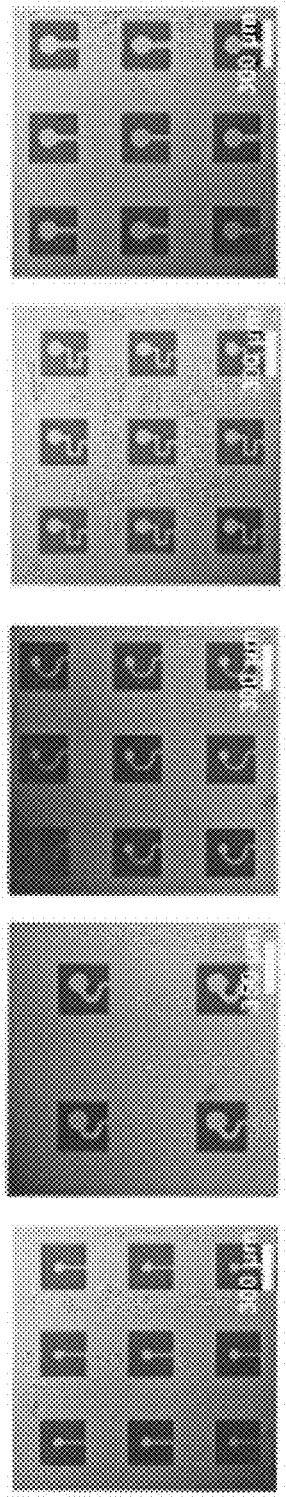

PATTERNED OPTOELECTRONIC TWEEZERS

CROSS REFERENCE TO RELATED APPLICATION

The present application claims priority to U.S. Provisional Patent Application Ser. No. 62/726,657, filed Sep. 4, 2018, the entire content of which is incorporated by reference herein as if set forth in its entirety.

TECHNICAL FIELD

The technical field generally relates to micromanipulation and confinement technologies using dielectrophoresis forces.

BACKGROUND

Optical micromanipulation technologies such as optical tweezers and optoelectronic tweezers (OET) have become popular for a variety of applications. In some applications, optical micromanipulation technologies are useful for studying, the behavior of microorganisms such as bacteria and C. elegans, for the evaluation of molecular dynamics and mechanics and the positioning and sorting of mammalian cells.

The first optical micromanipulation technology was demonstrated by Arthur Ashkin and colleagues in 1986 (A. Ashkin, J. M. Dziedzic, J. E. Bjorkholm, Opt. Lett. 1986, 11, 288. 23. D. G. Grier, Nature 2003, 424, 810), a method commonly known as "optical tweezers". In this technique, a high numerical aperture lens is used to apply an optical gradient force to an object, allowing for the transfer of optical momentum to control its position, "Optoelectronic tweezers" (OET) is a related but distinct technique that was first demonstrated by Ming Wu and colleagues in 2005 (P. Y. Chiou, A. T. Ohta, M. C. Wu Nature 2005, 436, 370. 5. M. C. Wu, Nat. Photon. 2011, 5, 322) and has subsequently been applied to manipulating nanowires, nanotubes, nanoparticles, dielectric beads and biological cells.

Referring to FIG. 1 (PRIOR ART), the structure of an OET device is schematically illustrated. The OET device includes transparent electrode parallel and a photoconductive electrode spaced apart to define a chamber therebetween, in which a solution containing particles to be micromanipulated is introduced. The transparent electrode is made of a thin layer of indium tin oxide (ITO), a transparent conductive material, coated on a glass substrate. The conductive electrode includes a thin layer of ITO further includes a thin layer of amorphous silicon (a-Si), a photoconductive material, successively coated on a glass substrate. An AC bias voltage is applied across the two electrodes, generating an electric field across the device. Light patterns are projected through the transparent electrode and focused on the amorphous silicon layer to change its electrical resistance, generating a dielectrophoretic force enabling the micromanipulation of the particles in the chamber.

Conventional OET devices are functional because of the unique characteristics of the photoconductive layer. In the dark, the impedance of the photoconductive layer is very high and the applied AC potential drops across this layer, leaving the solution in the chamber mostly field-free. However, when the device is illuminated, the impedance of the photoconductive layer is reduced significantly, such that the voltage drops predominantly across the solution above the illuminated area on the photoconductive layer. The resulting non-uniform electric field in the solution interacts with the target particles for micromanipulation in the solution, producing either repulsive (negative DEP) or attractive (positive DEP) force depending on the Clausius-Mossotti (CM) factors of the system.

Because OET relies on light to control the application of dielectrophoresis (DEP) forces rather than relying on the photons themselves to generate force, OET systems typically exert a much stronger manipulation force for a given intensity of light compared with optical tweezers. In addition, OET is particularly well suited for massively parallel manipulation schemes.

Although optical tweezers and OET are well-developed technologies with excellent precision and versatility for micromanipulation, they have potential shortcomings that limit their use for some applications. First, both techniques can cause physiological damage to trapped cells, by optical-induced heating from optical tweezers and photocurrent-induced Joule heating from OET. Second, in a standard micromanipulation platform that contains many micro-objects (beads, cells, etc.), it is challenging to generate a "clear" region that contains only the trapped micro-objects. Thus, when applying either technique to manipulate targeted particles in crowded environments, there is often unwanted physical/chemical/biological interference from other micro-objects in the field of view. Third, in both techniques, to maintain continuous application of the trapping force, the light source must always be "on." This exacerbates the first problem, above, and can also increase the evaporation rate of the liquid medium, thus altering the concentration of solutes and causing undesirable evaporation-induced fluidic shear forces.

There remains therefore a need for improvements to OET technology that alleviates at least some of the above-mentioned drawbacks.

SUMMARY

In accordance with one aspect, there is provided a patterned optoelectronic tweezers (p-OET) device, comprising:
  a top and a bottom electrode arranged in a parallel spaced apart relationship and forming a chamber therebetween; and
  a patterned photoconductor layer provided on the bottom electrode inwardly of said chamber, the patterned photoconductor layer forming a pattern comprising at least one raised region where the bottom electrode is coated by a photoconductor material and at least one hollow region where the bottom electrode is exposed, the pattern comprising one or more boundaries between the raised and hollow regions.

In some implementations, the top electrode and bottom electrodes each comprises a substrate coated with a conductive layer on a side thereof facing the other one of said top and bottom electrodes. The conductive layer of each electrode may be made of indium tin oxide or a metallic material.

In some implementations, the photoconductor material is hydrogenated amorphous silicon or Titanyl phthalocyanine.

In some implementations, the boundaries of the patterned photoconductor layer define a permanent trap feature.

In some implementations, the at least one raised region comprises a frame portion extending around a periphery of the bottom electrode, a trap portion extending within said frame portion and a circulation path joining the frame portion and the trap portion.

In some implementations, there is provided a p-OET device as above in combination with a voltage source connected to the top and bottom electrodes.

In some implementations, there is provided a use of a p-OET device as above n combination with and OET micromanipulation system to trap at least one particle.

In accordance with one aspect, there is provided a method for trapping a particle of interest comprising the steps of:
a) providing a patterned optoelectronic tweezers (p-OET) device comprising a top and a bottom electrode arranged in a parallel spaced apart relationship and forming a chamber therebetween, and further comprising a patterned photoconductor layer provided on the bottom electrode inwardly of said chamber, the patterned photoconductor layer forming a pattern comprising at least one raised region where, the bottom electrode is coated by a photoconductor material and at least one hollow region where the bottom electrode is exposed, the pattern comprising one or more boundaries between the raised and hollow regions defining a permanent trap feature;
b) introducing a solution containing the particle of interest the chamber of the p-OET device;
c) using an OET light trap, moving the particle of interest in the permanent trap feature of the p-OET device; and
d) stopping operation of the OET light trap.

In some implementations, the step of moving the particle of interest comprises projecting a ring-shaped light pattern onto the patterned photoconductor layer, a central area of said ring shaped light pattern defining the OET light trap.

In some implementations, the moving of the particle of interest further comprises scanning the ring-shaped light pattern over the raised regions of the patterned photoconductor layer.

In some implementations, the at least one raised region of the patterned photoconductor layer comprises a frame portion extending around a periphery of the bottom electrode, a trap portion extending within said frame portion and a circulation path joining the frame portion and the trap portion, and the scanning of the ring-shaped light pattern follows a trajectory from the frame portion to the trap portion through said circulation path.

In another aspect, there is provided an optoelectronic tweezers (OET) array, comprising a plurality of patterned optoelectronic tweezers (p-OET) device, each p-OET device comprising:
a top and a bottom electrode arranged in a parallel spaced apart relationship and forming a chamber therebetween; and
a patterned photoconductor layer provided on the bottom electrode inwardly of said chamber, the patterned photoconductor layer forming a pattern comprising at least one raised region where the bottom electrode is coated by a photoconductor material and at least one hollow region where the bottom electrode is exposed, the pattern comprising one or more boundaries between the raised and hollow regions.

In one aspect, there is provided a patterned optoelectronic tweezers (p-OET) device, comprising:
a top and a bottom electrode arranged in a parallel spaced apart relationship; and
a photoconductor layer provided on the bottom electrode, the photoconductor layer comprising at least one pattern formed therethrough along which the bottom electrode is exposed.

In some implementations, the pattern of the photoconductive layers defines a trap feature. In some implementations, a use of a such a p-OET device in combination with and OET micromanipulation system to trap at least one particle.

In one aspect, there is provided a method for trapping a particle of interest, comprising the steps of:
providing a p-OET device where the patterned photoconductor layer includes a trap feature;
using an OET light pattern, moving the particle of interest in the trap feature of the p-OET device; and
stopping operation of the OET light pattern.

Other features and aspect of the invention will be better understood upon reading of embodiments thereof with reference to the appended drawings.

BRIEF DESCRIPTION OF THE DRAWINGS

The patent or application file contains at least one drawing executed in color, Copies of this patent or patent application publication with color drawings will be provided by the Office upon request and payment of the necessary fee.

FIGS. 3A to 3E are bright-field microscope images of p-OET devices according to various embodiments.

FIGS. 5A and 5B are bright-field microscope images of a bead in a light trap in a conventional OET device. FIGS. 5C and 5D are bright-field microscope images of the same bead in a same light trap on a p-OET device including a linear boundary. FIGS. 5E and 5F are graphical illustration of the force profiles measured for a 25-μm-diameter bead at different displacements with respect to the boundary of FIGS. 5C and 5O, when the p-OET device is driven at 7 V p-p and 20 Vp-p, respectively. FIGS. 5G and 5H show the simulated electrical potential distribution and the simulated electrical field distribution in the p-OET device.

FIG. 6A to 6C are bright-field microscope images illustrating the formation of a is light-induced image in a suspension of polystyrene beads representing a stylized cartoon of Albert Einstein. FIG. 6D to 6F are bright-field microscope images of the beads 1.5, 3, and 6 min after patterning, illustrating the degradation of the pattern with time if no light is applied to maintain the dielectrophresis force.

FIGS. 8A to 8L are bright-field microscope images illustrating the trapping of polystyrene beads in a p-OET trap according to one embodiment.

FIG. 9A to 9M are bright-field images showing the selection and storage of MCF-7 breast cancer cells (pre-labelled green by CellTracker dye) and ARPE-19 human retinal pigment epithelial cells (pre-labelled red by CellTracker dye) in p-OET traps.

FIGS. 10A to 10E are bright-field images of arrays of p-OET devices according to embodiments.

DETAILED DESCRIPTION

In accordance with some aspects, there are disclosed patterned Optoelectronic Tweezers devices (hereinafter referred to as p-OET devices) and uses thereof.

In some implementation, the photoconductive layer typically found on a conventional OET device is patterned in a p-OET device, which enables convenient integration of OET with conventional dielectrophoresis (DEP). In some embodiments, the new p-OET format permits flexible, light-pattern-driven manipulation of particles/cells across an X-Y plane, and also includes micro-patterned electrode coatings that can permit continuous trapping of is particles and cells by DEP, even after the light source is turned "off." In some examples described here, the forces exerted by the patterned photoconductor were found to be useful to (a) push away unwanted particles/cells (allowing for a clear field of experimentation), and to (b) keep the particles/cells immobilized for long-term after moving them to the targeted areas. It will however be understood that p-OET may find use in a wide range of applications in the area of micromanipulation.

In some embodiments, the p-OET devices described herein may be used for the same fields of application as traditional OET devices and others. Examples of applications include the study of the behavior of microorganisms such as bacteria and *C. elegans*, the evaluation of molecular dynamics and mechanics, the positioning and sorting of mammalian cells, the study of cell-cell interactions, single cell selection and lysis, pharmacodynamic test, biochemical assay, assembly of electronic and photonic components, and the like.

p-OET Device

Figure 1:
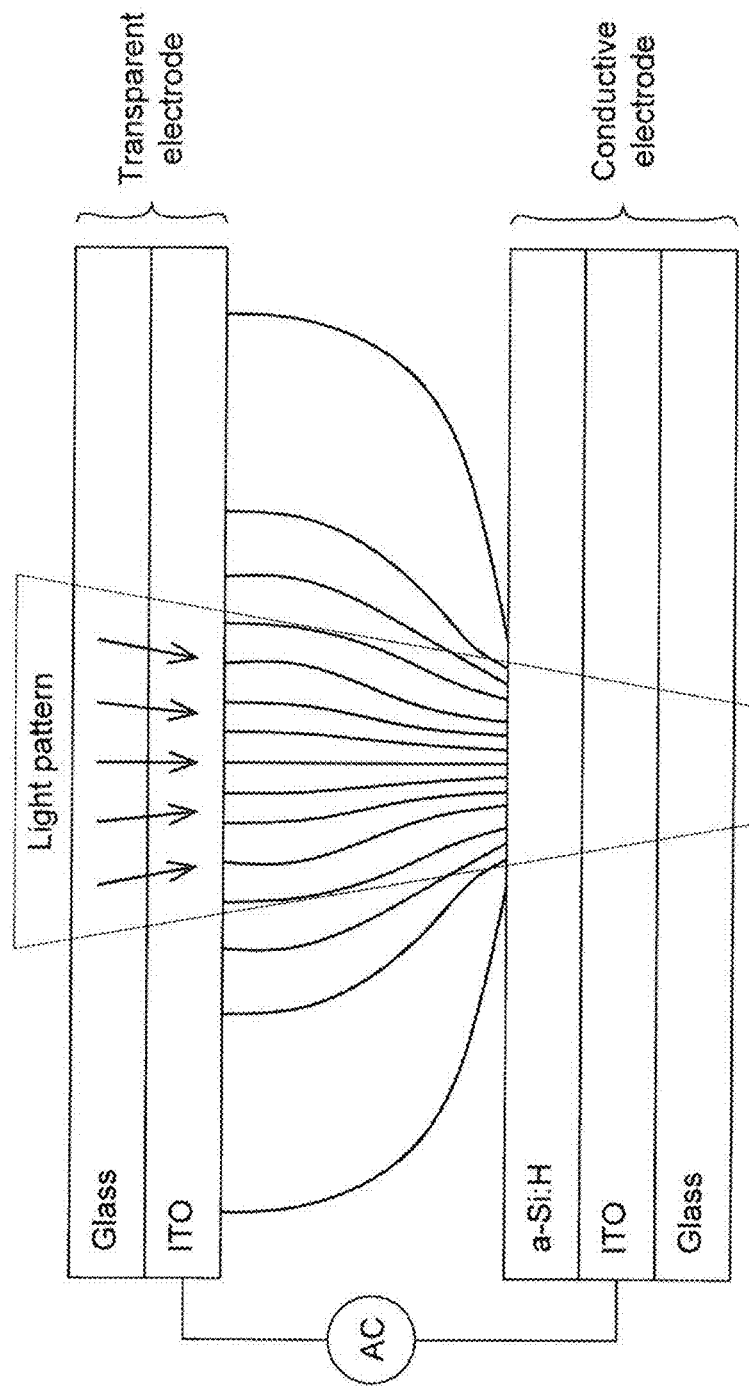
FIG. 1 (PRIOR ART) is a schematic representation of the operation of a conventional OET device.
Figure 2:
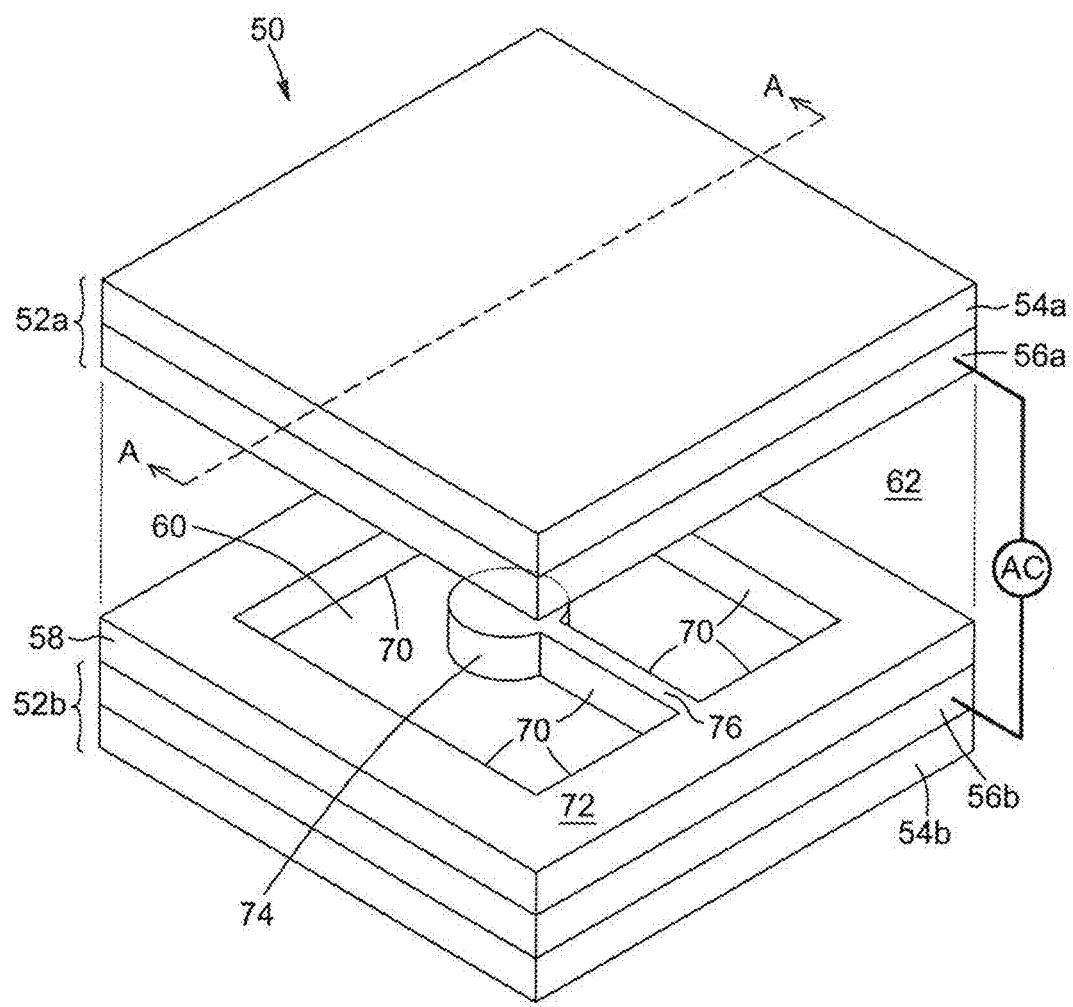
FIG. 2 is a 3D side elevation representation in partial transparency of a p-OET device according to one embodiment.
Figure 2A:
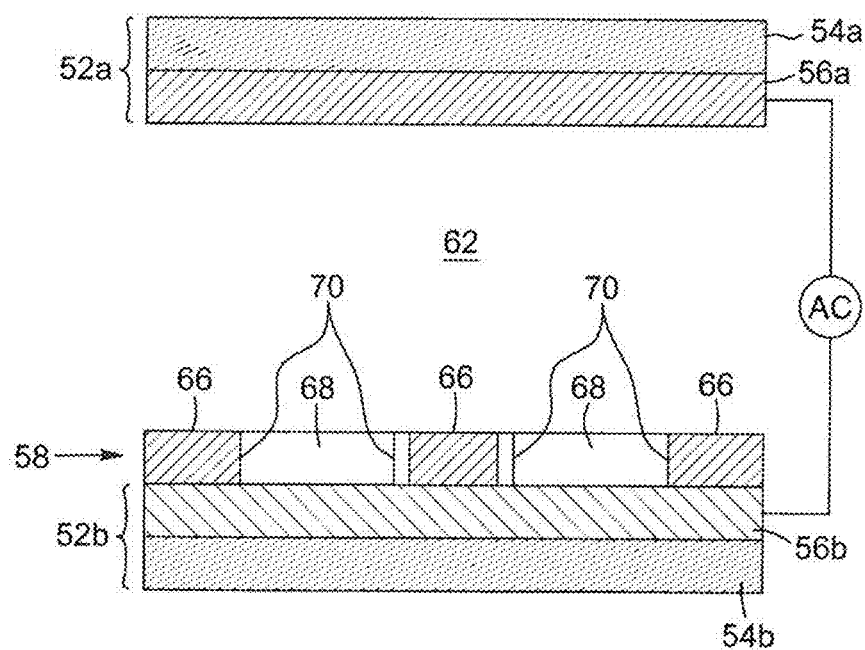
FIG. 2A is a cross-sectional representation taken across lines A-A of FIG. 2.

Referring to FIGS. 2 and 2A, there is shown a p-OET device 50 according to one implementation.

The p-SET device 50 includes a top electrode 52*a* and a bottom electrode 52*b* arranged in a parallel spaced apart relationship. Each of the top and bottom electrode includes a substrate 54*a*, 54*b* made of glass or other suitable material, coated on one side with a thin conductive layer 56*a*, 56*b*. In typical implementations, each conductive layer 56*a*, 56*b* is made of indium tin oxide (ITO), and the conductive layer is also referred to below as an ITO layer. It will however be understood that other materials having appropriate conductive properties may be used without departing from the scope of protection. For example, the conductive layers 56*a*, 56*b* may be made of metallic materials such as silver, gold, copper, and the like. The free space or volume between the top and bottom electrodes 52*a*, 52*b* forms a chamber 62 within which the manipulation of particles/cells may be performed, as will be explained further below.

The p-OET device 50 further includes a patterned photoconductor layer 58 provided on the bottom electrode 52*b*, inwardly of the chamber 62. The photoconductor layer 58 forms a pattern 60 which includes at least one raised region 66 where the bottom electrode 52*b* is coated by a photoconductor material, and at least one hollow region 68 where the bottom electrode 52*b* is exposed. The pattern 60 also includes one or more boundaries 70 between the raised sand hollow regions 66 and 68. The patterned photoconductor layer 58 may deposited as a uniform layer then etched to remove material in the areas of the hollow regions 68.

In some implementations, the photoconductor material of the patterned photoconductor layer 58 may be hydrogenated amorphous silicon (a-Si:H). It will however be understood that other photoconductor materials in which the resistance of the material drops after being illuminated with light may also be used, such as for example Titanyl phthalocyanine pigments (TiOPc). In typical embodiments the patterned photoconductor layer 58 may have a standard thickness along the raised regions 66 of 1 μm. In other variants, the thickness of the patterned photoconductor layer 58 can range between about 100 nm to 2 μm. The pattern 60 provided in the photoconductor layer 58 can define any of a multitude of shapes, examples of which are provided further below.

In use, an AC potential is applied between the top and bottom electrodes 52*a*, 52*b* of the p-CET device 50. A voltage source 64 is connected to the ITO layers 54*a*, 54*b* of the respective top and bottom electrode to apply the AC potential. The voltage source may be part of the p-OET device 50 or may be provided in combination therewith, for example as part of a micromanipulation system in which the p-OET device is integrated.

In some implementations, the p-OET device may be fabricated using known techniques. By way of example, for the exemplary devices mentioned herein, the top electrode is a glass slide coated on one side with 200-nm-thick ITO (Riley Supplies). The bottom electrode is formed from an ITO-coated glass slide, with the ITO layer coated with 1-μm-thick a-Si:H photoconductive layer, deposited by plasma enhanced chemical vapor deposition (Oxford Instruments Plasmalab 180 ICP-CVD system) from silane gas (30 sccm) at 250° C. with 10 W input power at 10 mTorr pressure. Micro-patterns in the photoconductive layer were formed by standard photolithography and etching processes. Briefly, positive photoresist (Microposit S1818) was spin-coated onto the a-Si—H layer, and then exposed to UV light through a photomask to define the micro-patterns. Substrates were then immersed in developer (Microposit MF-312) to form patterns in the photoresist. After rinsing, drying, and post-baking, the substrates were transferred to a ICP-RIE system (Oxford Instruments PlasmaPro-100 Cobra ICP-RIE System) to remove the a-Si:H (exposing ITO) in exposed regions using SF6 gas (200 sccm flow rate, 1500 W ICP power, 20 W forward power, 20 mTorr pressure, 0° C. temperature; etch rate: 0.1 μm/1.2 sec). After etching, the remaining photoresist was removed. Prior to assembly, approximately 2 mm$^2$ of the a-Si:H material at the edge of the photoconductive layer was removed with a blade to expose the conductive ITO layer. Electrical leads were interfaced with the ITO layers on both electrodes via conductive silver paste (ALDRICH 735825) and waterproof epoxy (Permatex 84111).

Devices were assembled by joining a top electrode with a bottom electrode by adhering tier to a 150-μm-thick spacer (3M 9965) to form an enclosed chamber. Each device was then affixed to a standard microscope glass slide and was positioned in the slide holder of the microscope.

In some implementations, there is provided an OET array comprising a plurality of p-OET devices such as described above. FIGS. 10A to 10E show examples of such array.

Micromanipulation System

Figure 4:
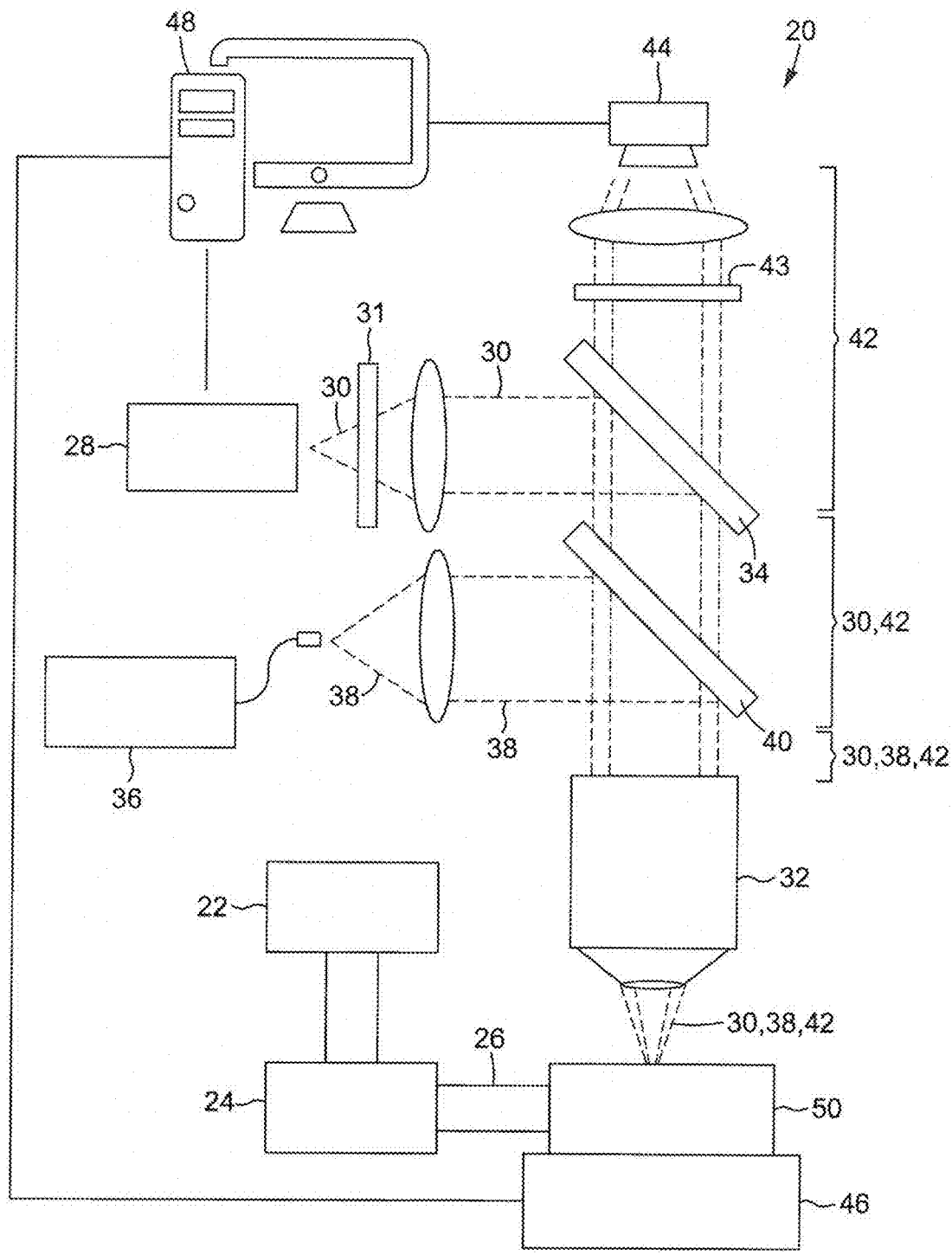
FIG. 4 is a schematic representation of micromanipulation system.

Referring to FIG. 4, in some implementations, there is provided a micromanipulation system 20 including a p-OET device 50 such as described herein used in combination with traditional OET techniques. The system may be similar to known systems using conventional (unpatterned) OET devices.

In the illustrated embodiment, the micromanipulation system 20 includes a function generator 22 and amplifier 24 providing an AC potential 26 to drive p-OET device 50. In some implementations, the micromanipulation system 20 further includes a digital micro-mirror device (DMD) projector 28 generating light patterns 30. As known in the art, light patterns may be used to move and/or confine particles in an OET device. The DMD projector 28 may be a light pattern generator. Other types of DMD projectors may be used in other variants, such as for example spatial light modulators and micro-LED displays. The light patterns 30 are projected onto the p-OET device 50, for example through an objective 32 of an upright microscope (not shown). It will be readily understood that objectives of different types may be used. In the illustrated configuration the micromanipulation system includes a first beam splitter 34 disposed in a path of the light patterns 30 from the DMD projector 28 and reflecting at least a portion of these light patterns 30 towards the objective 32 at a 90 degree angle with respect to the MID projector 28.

The micromanipulation system 20 further includes an illumination source 36 projecting an illumination beam 38 onto the p-OET device 50. The illumination light source 36 may for example, be embodied by a fluorescent light source or the like. The illumination beam 38 may be coupled into the objective 32 by a second beam splitter 40. Return light 42 from the p-OET device 50 traverses the objective 32 and both beam splitters 40, 34 and is collected by a CCD camera 44.

It will be understood that the system may include any suitable optical components for shaping, redirecting, focusing, filtering or otherwise affecting the light patterns 30, the illumination beam 38 and the return light 42. By way of example, also in the illustrated embodiment, the micromanipulation system 20 includes a long-pass filter 31 disposed between the DMD projector 28 and the first beam splitter 34. The long-pass filter 31 preferably has a transmission profile configured to remove blue wavelengths from the light patterns 30 prior to projecting into the microscope. The illustrated micromanipulation system 20 may also include a short-pass filter 43 positioned in front of the CCD camera 44 to reduce the intensity of red wavelengths in emission from the DMD projector 28, allowing a clear view of manipulated particles or cells in the p-OET device 50 juxtaposed with a faint image of the light, patterns 30.

In the illustrated embodiment, the position of the p-OET device 50 is controlled by a motorized positioning stage 46. The motorized positioning stage, DMD projector 28 and COD camera 44 are preferably controlled by a controller 48 such as a computer or other device or combination of devices, allowing centralized control and monitoring of the micropositioning system 20.

In the experiments described below, a micromanipulation system such as shown in FIG. 4 was used, and included a digital micro-mirror device projector (Dell 1650) as the DMD projector. The objective was part of an upright fluorescent microscope (Leica DM 2000). The micromanipulation system also included a fluorescent excitation source (X-cite 120), a motorized stage (Märzhäuser Scan Plus 100×100), a high-resolution stepper motor controller (Märzhäuser TANGO), a control joystick (Märzhäuser 3-axes joystick), an amplifier (Thurlby Thandor Instrument WA31), a function generator (Agilent 33220A), a charge-coupled device camera (LW Scientific MiniVID; ToupView image software) and a Desktop computer (Dell Optiplex 790). The filters in the system include a long-pass filter (Thorlabs FD1R) and a short-pass filter (Thorlabs FES0550) An infrared camera (FUR E60) was used to measure the temperature profiles of the p-OET device. A power meter with a silicon photodiode detector (Thorlabs PM16-130) was used to measure the optical power from the projector. A conductivity meter (HACH H270G) and probe (HACH PH77-SS) was used to measure the conductivity of medium. Preparation of particle suspension involved the following: for spherical polystyrene beads with diameters of 15 µm, 20 µm, and 25 µm (Polysciences) were suspended in deionized (DI) water containing 0.05% (v/v) Tween 20 (P9416 SIGMA). The conductivity of the suspension was measured to be 5.0 mS/m. In a typical experiment, a 15 µL of the suspension was pipetted into the chamber of the p-OET device. For cell culture and fluorescent labelling: MCF-7 cells were maintained in Dulbecco's modified Eagle's medium (DMEM; Life Technologies) supplemented with 10% (v/v) fetal bovine serum (FBS; Gibco) and 1% (v/v) penicillin and streptomycin (pen./strep., invitrogen), ARPE-19 cells were maintained in DMEM/F12 media (Life Technologies) supplemented with 10% (v/v) FBS and 1% (v/v) pen./strep. Cells were incubated in a humidified 5% CO2 air environment at 37° C. Adherent cells were stained by adding 10 µM CellTracker Green CMFDA or Red CMPTX (ThermoFisher Scientific), diluted in the cell line's base media in the absence of serum, and incubated for 30 minutes at 37° C. Stained cells were then washed twice by addition of Phosphate-Buffered Saline (PBS, Life Technologies), passaged using 0.25% Trypsin-EDTA (Life Technologies) and re-suspended in sucrose media (9 wt % sucrose, 0.3 wt % D-Glucose, 1.25% v/v PBS; conductivity measured to be 22.1 mS/m) at a density of 0.1-1×106 cells/mL. After filtering the sucrose media containing cells through a 40-µm-diameter pore strainer (Falcon), an aliquot of cell-suspension (15 µL) was pipetted into the chamber of OET device for experiments.

In typical experiments, micro-objects were manipulated by OET and p-OET by applying AC potentials (7 Vp-p, 20 Vp-p, or 25 Vp-p at 25 kHz) between the top and bottom electrodes, respectively, with light patterns projected through a 10× objective. In most experiments, the light patterns were held stationary while the microscope stage was translated; in other experiments, the stage was held stationary while the light patterns were moved by projecting moving animations onto the field of view Particle Behavior in p-OET Manipulations In accordance with some implementations, the pattern 60 of the photoconductive layer 58 defines a permanent trap feature.

Traditional OET devices provide for the micromanipulation of particles solely through forces generated from the pattern of light projected onto the bottom electrode, which is coated with an even (unpatterned) photoconductor layer. It is known in the art to shape the light patterns projected through the OET device to form a light trap in which the micromanipulated particles are confined. By way of example, referring to FIGS. 5A and 5B (PRIOR ART) it is, known to use light patterns forming a "doughnut" shape or ring in the plane of the photoconductor layer in traditional OET, such that the DEP forces confine the particles to the central area of the ring. Once the light pattern is removed or turned "off", the trapping effect disappears and the particles are once again free to move about within the chamber.

With reference to FIGS. 6A to 6C, the process of trapping 10-µm-diameter polystyrene beads in a standard OET device (without a patterned layer) to form an 'Einstein' cartoon pattern at an AC potential of 7 Vp-p is shown.

FIG. 6A is an image of the solution in the OET device prior to the projection of the light patterns. FIG. 6B shows the image of the cartoon obtained by positioning the polystyrene beads in the chamber through illumination of the photoconductor layer using suitable light patterns. The polystyrene beads experience a negative DEP force and move away from the illuminated regions, becoming trapped within the dark areas in the light patterns. FIGS. 6C to 6F are bright-field microscope images of the beads after 10 sec, 1.5 min, min, and 6 min respectively, illustrating the degradation of the pattern with time. As can be observed, the image persists for a short time after the light is turned off, but as time passes, the image gradually degrades and becomes unrecognizable. This sequence illustrates a common problem in optical micromanipulation. It is desirable to limit the duration of illumination to avoid potentially deleterious effects to the trapped, micro-objects. However, when the light is turned "off," objects in the device are subject to competing forces (Brownian motion, diffusion, fluid movement effects, etc.) that "undo" the work of the manipulation.

By contrast, in a p-OET device such as described herein the boundaries between raised and hollow regions of the patterned photoconductor layer form a permanent trap feature, which in essence is always "on," regardless of the state or presence of the projected light.

Referring to FIGS. 5A through 5I, several experiments were performed to characterize particle behavior in a p-OET device according to one embodiment. The p-OET device and micromanipulation system described above were used. The light patterns generated by the DMD generator formed a 'doughnut'-shaped or ring-shaped light trap such as used in conventional OET. The ring shape of the light patterns had an inner radius of 80 µm and an outer radius of 150 µm, such that a single polystyrene particle can be trapped is in the central (non-illuminated) region, confined within the circular ring of light by a negative DEP. To calibrate the force applied to a particle in this light trap, a series of experiments in a conventional OET device were completed, in which the stage velocity was gradually increased to control the speed of trapped particle. For example, FIGS. 5A and 5B (PRIOR ART) show representative microscope images of a 25-µm-diameter polystyrene bead in the OET doughnut light trap travelling at 60 µm/s and 10 µm/s, respectively. As shown, the bead moves toward the edge of the light pattern as the velocity increases, indicating that a stronger DEP force is exerted to balance the increasing viscous drag force, allowing the bead to maintain a larger velocity. Stated another way, when velocity is increased, the bead moves closer to the edge of the light pattern, a phenomenon that can be quantified by the center-to-center displacement in the OET trap, 'DO'.

To study the properties of p-OET, an additional series of experiments was completed in which a 25-µm-diameter polystyrene bead was trapped by the same OET doughnut light trap described above over a raised region of photoconductor material, and was moved perpendicularly toward a linear boundary between the raised region and a hollow region of exposed ITO. In other words, in this implementation the patterned photoconductor layer was a line of removed a-Si:H, i.e., a simple linear p-OET feature. The light trap movement velocity in these experiments was low (2 µm/s); thus, under standard OET conditions, the bead remains near center of the light trap (with small DO). This behavior changes when the bead is driven toward the p-OET boundary. A new parameter, 'DP', was assigned to quantify the distance between the center of the bead and the boundary to evaluate this change in behavior. FIGS. 5C and 5D show microscope images of the bead as the doughnut light trap is moved toward the boundary, with DP=100 µm (when the bead is far from the boundary) and DP=46 µm (when the bead is closer to the boundary), respectively. As shown, as the bead gets closer to the exposed ITO, it is pushed away from the center of the OET doughnut light trap. That is, as DP is made to decrease (by moving the microscope stage), DO increases, under conditions in which DO would otherwise remain small and constant. The change in DO in these experiments is thought to be a result of the competition between the OET force in the light pattern and the DEP force generated at the boundary of the exposed ITO.

The force generated by an OET light pattern on a bead can be calculated based on the light trap profile and the position of the bead in the light trap which can, in turn, allow the calculation of the DEP force generated by the boundary between the raised regions and the hollow regions of the photoconductor layer. Therefore, a force profile can be plotted for the bead when it has different displacement DP resulting from being close to the p-OET boundary. Referring to FIGS. 5E and 5F, there is shown a graphical illustration of the force profiles measured for a 25-µm-diameter bead at different displacements with respect to the ITO/a-Si:H boundary when the p-OET device is driven at 7 V p-p (FIG. 5E) and 20 Vp-p (FIG. 5F), respectively. As shown, the DEP force generated by the ITO/a-Si:H boundary increases as the displacement DP decreases, indicating that the DEP force repelling the bead increases as it approaches the ITO/a-Si:H boundary.

To better understand the observed experimental results, numerical simulations were carried out in COMSOL Multiphysics based on a well-developed 2D simulation model. The model incorporated the XZ cross-section of the p-OET device. FIG. 5G shows the simulated electrical potential distribution in the p-OET device. As shown in the simulation, there is a large electric potential variation along Z-axis (between the top and bottom electrodes) above the hollow region without the a-Si:H layer, caused by the conductivity difference between ITO and a-Si:H. This effect also induces a large electric potential variation along the X-axis at the ITO/a-Si:H boundary region above the bottom electrode. FIG. 5H shows the simulated electrical field distribution in the p-OET device. As shown in the simulation, there exist strong electric fields (above $1\times10^6$ V/m) and field variations at the ITO/a-Si:H boundary. The force profiles of the bead at different displacements with respect to the ITO/a-Si:H boundary were simulated using classic DEP theory and the dipole approximation method, as shown in FIGS. 5c and 5D (solid line). After scaling, the simulation had a good qualitative match to the data, suggesting that there exists a strong DEP force to repel the bead at the ITO/a-Si:H boundary caused by the non-uniform electric field.

p-OET Traps

In accordance with some implementations, p-OET devices may be configured to provide p-OET "traps" allowing the permanent trapping, i.e. storing, confining, or localizing of particles at a specific location within the chamber. The p-OET traps described herein are understood to result from the DEP forces generated at the boundaries of the photoconductor pattern, and are to be contrasted with the OET light traps which are light-induced and tend to dissipate after the light stimulation is removed, as explained above.

Figure 7A:
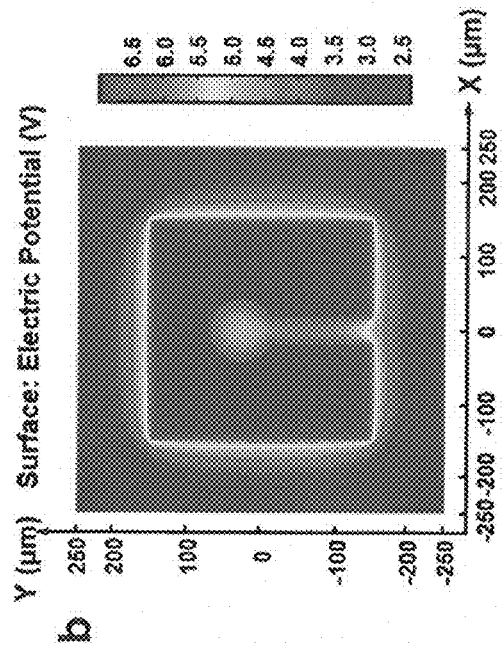
FIG. 7A is a schematic representation of a p-OET device comprising a permanent trap.
Figure 7B:
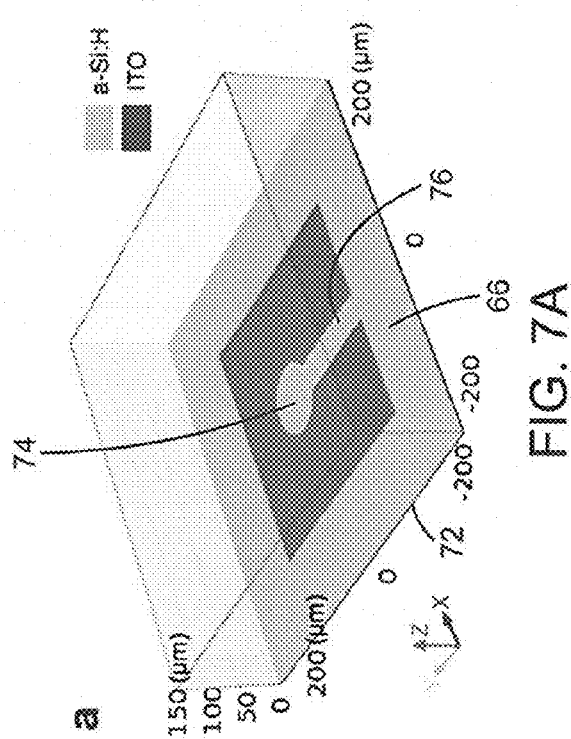
FIGS. 7B and 7C show respectively the simulated electric potential distribution and the electric field distribution for the device of FIG. 7C driven at driven at 7 Vp-p.
Figure 7D:
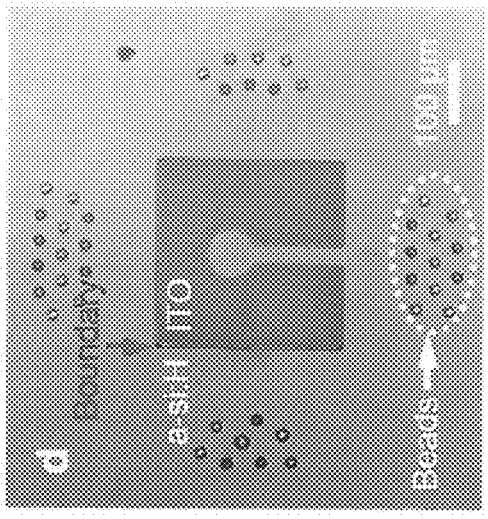
FIG. 7D is a bright-field microscope image of the device of FIG. 7A showing the influence of the p-OET trap on 20-μm-diameter beads located outside of the trap.
Figure 7C:
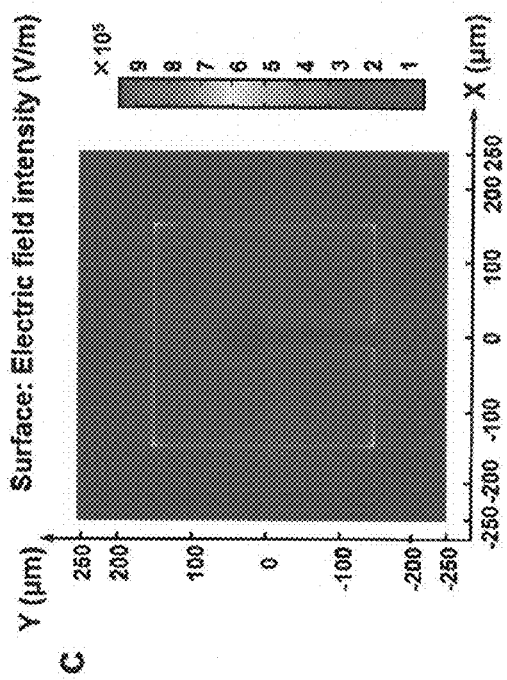

Referring to FIG. 7A, there is shown an example of a p-OET device in which the pattern of the photoconductive layer defines a permanent trap feature. In this example, the raised regions 66 of the patterned photoconductor layer includes a frame portion 72 which extends around the periphery of the bottom electrode, an trap portion 74 extending inside the frame portion 72 and a circulation path 76 joining the frame portion 72 and the trap portion 74. In the illustrated example the trap portion is circular and positioned at the center of the pattern, but other shapes and, positions may be envisioned. A 3D model was developed to simulate this system, with length (X-axis) and width (Y-axis) set to 250 µm and height (Z-axis) set to 150 µm. Electric potential distribution and electric field distributions were simulated and are shown in FIGS. 7A and 7B, respectively (XY-slices at Z=1.3 µm, i.e. for a bead located 0.1 µm above the a-Si:H layer). As indicated, the electric potential varies significantly at the region near the ITO/a-Si:H boundary 70, inducing a strong electric field gradient directly over the boundary 70. This 3D model is consistent with the 20 simulations shown in FIGS. 5g and 5H, indicating there exists a strong DEP force surrounding the p-OET trap, both within the trap portion 74 and along the frame portion 72. As shown in FIG. 7D, when a p-OET trap was exposed to 20-µm-diameter polystyrene beads outside of the trap, the beads were repelled from the outer ITO/a-Si:H boundary. Hence, in some variants the p-OET device may provide the capacity to clear regions of the device of unwanted particles (e.g., beads or cells), keeping the patterns free for "trapping".

It will be readily understood that the pattern 60 of the patterned photoconductor layer may define different shapes without departing from the scope of the invention. Referring to FIGS. 3A to 3E, there are shown variants of such patterns where the trap portion 74 has different sizes and positions. In other variants (not shown), the trap portion may have a non-circular shape, such as for example square, rectangular, triangle, polygon, etc or any other shape resulting in DEP forces confining particles at a specific position or within a specific area. The embodiments of FIGS. 3A to 3E also illustrate different trajectories for the circulation path 76, by way of example only. The pattern 60 may alternatively define multiple trap portions positioned wherever the trapping of particles is desired.

Trapping of a Particle of Interest

In some implementations, p-OET devices including p-OET permanent trap features as described above may be combined with an OET light trap to select and move individual beads into the permanent trap using light-induced DEP 3D force. A p-OET device according to any one of the variants described herein may therefore be used in combination with and OET micromanipulation system to trap at least one particle.

In accordance with one aspect, ere is provided a method for trapping a particle of interest.

The particle of interest may be any microscopic body apt to be moved by OET. The particle may for example be polystyrene microspheres, silica microspheres, Poly (methyl methacrylate) (PMMA) microspheres, ceramic microspheres, silicon microspheres, or the like. The reference to "beads" in the section below is used as shorthand and is not meant to be limitative to the type of particles which may be micromanipulated using the present method.

The method first includes providing a p-OET device. As described above, the p-OET device includes a top and a bottom electrode arranged in a parallel spaced apart relationship and forming a chamber therebetween, and further comprising a patterned photoconductor layer provided on the bottom electrode inwardly of the chamber. The patterned photoconductor layer forms a pattern comprising at least one raised region where the bottom electrode is coated by a photoconductor material and at least one hollow region where the bottom electrode is exposed. The pattern comprising one or more boundaries between the raised and hollow regions defining a permanent trap feature.

The method next includes introducing a solution containing the particle of interest in the chamber of the p-OET device.

The method next includes moving the particle of interest in the permanent trap feature of the p-OET device, using an OET light trap. In one embodiment, this may be accomplished by generating a ring-shaped light pattern onto the patterned photoconductor layer, a central area of the ring shaped light pattern defining the OET light, trap. The OET light trap may also be any other light pattern which may act on the particle to move it within the p-OET device. For example, light patterns such as square, rectangular, triangle, polygon or any other shapes with a dark central region and an illuminated border.

It will be readily understood that in other embodiments The ring-shaped light pattern is scanned over the raised regions of the patterned photoconductor layer. In some implementation the patterned photoconductor layer includes a frame portion extending around a periphery of the bottom electrode, a trap portion extending within said frame portion and a circulation path joining the frame portion and the trap portion, and the scanning of the ring-shaped light pattern follows a trajectory from the frame portion to the trap portion through the circulation path.

The method finally includes a step of stopping operation of the OET light trap. As explained above, the DEP forces at the boundary between the raised and hollow regions of the photoconductor layer, especially around the trap portion, will ensure that the particle remains in position within the trap portion once the light pattern is turned off.

An example of implementation of the method above is shown in FIGS. 8A to 8L.

FIG. 8A shows the microscope image of a 15-µm-diameter bead in an OET doughnut or ring-shaped light trap outside of a p-OET permanent trap feature, defined by the trap portion of a pattern having a configuration such as described above. FIG. 8B shows a microscope image of the same bead after it has been moved into the center of the p-OET trap feature, with a dashed line indicating the path that was taken. To accomplish this task, the microscope stage of the microsystem illustrated in FIG. 4 was controlled to follow the indicated path. Interestingly, the movement of the OET light trap does not have to perfectly track the trajectory defined by the raised portions of the photoconductor layer. After being moved over the trap portion, the bead remains in the center of the path, presumably avoiding high negative DEP forces along the edges. As shown in FIGS. 8C and 8D, by repeating this process, multiple beads can be moved into the same p-OET permanent trap along the same track. After the beads are moved into the p-OET permanent trap, they are preserved and confined even after the projector of the OET light trap was turned off. This confinement is enabled by the "always on" DEP force generated by the circular ITO/a-Si:H boundary of the trap.

FIGS. 8E to 8L is a compendium of representative microscope images demonstrating the capacity to select and store multiple beads in p-OET traps with different geometries, according to embodiments of the present method. As shown, the beads adopt symmetrical patterns centered in the middle of the circular portion of the p-OET trap. This effect is reproducible—when the same number of beads is stored in a trap with the same geometry, the resulting shape adopted by the beads is reproducible. It is speculated that the shapes formed are determined by the distribution of DEP force on the central trap region. This region of the device can be modelled as a potential well with the energy level gradually decreasing from the edge (i.e., the interface between exposed ITO and the pattern) to the center. A single bead in the trap can be approximately regarded as an electric dipole, which positions itself at the minimum energy level near the center of the trap region. When multiple beads are moved into the same trap, they form a multi-dipole system with each dipole being influenced not only by the boundary of the trap region but also by the other dipoles in the system. Thus, the multi-dipole system reproducibly arranges itself to reach an electrostatic equilibrium, keeping the energy of the system at the minimum level.

In some implementations, the method may be used to separate and isolate a particle of one type from particles of other types. in some implementations, the method may be used to trap multiple particles within the same p-OET trap or within different p-OET traps. In some implementations the method may further include a step of extracting the particle from the p-OET trap, or extracting other particles from the trap after a transformative process. By way of example the method may be used in the context of sorting, preservation and extraction of specific cell types from multicellular populations.

The trapping of the particle is advantageously permanent, in the sense that the particle remains substantially in place after the OET light pattern is removed. In some implementation, this trapping effect remains at least within a time scale sufficient to performed desired tests, procedures, transformations etc, on the particle as warranted by the application. The conservation of the confinement properties of the trap may be last for at least several weeks.

Example of Micromanipulation of Cells

OET has been heralded for its capability to precisely control the positions of mammalian cells. In some implementations, p-OET devices may be useful in the context of such applications. By way of example, MCF-7 human breast cancer cells and ARPE-19 human retinal pigment epithelial cells were used as a model system to evaluate this capability. Under the conditions used here, these cells experience a negative light-induced DEP force (like the beads described above), such that they can be manipulated by the doughnut-shaped OET light trap described above.

FIGS. 9A to 9D shows microscope images depicting the selection and movement in OET light traps of two cells to be stored in a p-OET permanent trap. As is the case for dielectric beads, this method is useful for selection and storage of cells in p-OET traps with a variety of formats, as shown in the bright-field/fluorescent microscope images FIGS. 9D to 9M. In some cases, a "half" doughnut light pattern instead of a "whole" doughnut light pattern is used for cell manipulation, a practice that was found to minimize the influence of the light pattern on cells that had previously been moved into the trap.

As shown, p-OET can provide a useful new tool for selecting and isolating groups of mammalian cells. In some implementations, it, may be appropriate for controlled cell mixing experiments to study biological processes such as entosis-mediated, cell competition, whereby cancer cells invade proximate healthy cells, resulting in the death of the latter. Likewise, embodiments of the p-OET devices may be useful for controlled study of processes such as immune cell interactions within cancer microenvironments, as well as immune cell-cancer cell interactions. Some applications involving cells may need to reconcile the difference between the low-conductivity media (required for the techniques described here) and conventional, high-conductivity media that are typically used for long-term cell culture and maturation. Techniques for automated switching between high/low-conductivity media have been reported for OET and other techniques.

Of course, numerous modifications could be made to the embodiments described above without departing from the scope of the invention.

The invention claimed is:

1. A patterned optoelectronic tweezers (p-OET) device, comprising:
   a top and a bottom electrode arranged in a parallel spaced apart relationship and forming a chamber therebetween; and
   a patterned photoconductor layer provided on the bottom electrode inwardly of said chamber, the patterned photoconductor layer forming a pattern comprising at least one raised region where the bottom electrode is coated by a photoconductor material and at least one hollow region where the bottom electrode is exposed, the pattern comprising one or more boundaries between the raised and hollow regions, said boundaries defining a light-independent dielectrophoresis trap feature.

2. The p-OET device according to claim 1, wherein each of the top electrode and bottom electrodes comprises a substrate coated with a conductive layer on a side thereof facing the other one of said top and bottom electrodes.

3. The p-OET device according to claim 2, wherein the conductive layer of each electrode is made of indium tin oxide or a metallic material.

4. The p-OET device according to claim 1, wherein the photoconductor material is hydrogenated amorphous silicon or Titanyl phthalocyanine.

5. The p-OET device according to claim 1, wherein the at least one raised region comprises a frame portion extending around a periphery of the bottom electrode, the light-independent dielectrophoresis trap feature extending within said frame portion, the at least one raised region further comprising a circulation path joining the light-independent dielectrophoresis trap feature to the frame portion.

6. The p-OET device according to claim 1, in combination with a voltage source connected to the top and bottom electrodes.

7. Use of a p-OET device according to claim 5, in combination with an optoelectronic tweezers micromanipulation system to micromanipulate at least one particle from the frame portion to the light-independent dielectrophoresis trap feature along the circulation path.

8. The p-OET device according to claim 1, said boundaries further defining a circulation path leading to the light-independent dielectrophoresis trap feature.

9. A method for trapping a particle of interest, comprising the steps of:
   a. providing a patterned optoelectronic tweezers (p-OET) device comprising a top and a bottom electrode arranged in a parallel spaced apart relationship and forming a chamber therebetween, and further comprising a patterned photoconductor layer provided on the bottom electrode inwardly of said chamber, the patterned photoconductor layer forming a pattern comprising at least one raised region where the bottom electrode is coated by a photoconductor material and at least one hollow region where the bottom electrode is exposed, the pattern comprising one or more boundaries between the raised and hollow regions defining a light-independent dielectrophoresis trap feature;
   b. introducing a solution containing the particle of interest in the chamber of the p-OET device;
   c. applying an AC voltage between the top and bottom electrodes of the p-OET device;

d. using an optoelectronic tweezers light trap, moving the particle of interest in the light-independent dielectrophoresis trap feature of the p-OET device; and e. stopping operation of the OET light trap.

10. The method according to claim 9, wherein the step of moving the particle of interest comprises projecting a ring-shaped light pattern onto the patterned photoconductor layer, a central area of said ring shaped light pattern defining the OET optoelectronic tweezers light trap.

11. The method according to claim 10, wherein the moving of the particle of interest further comprises scanning the ring-shaped light pattern over the raised regions of the patterned photoconductor layer.

12. The method according to claim 11, wherein the at least one raised region of the patterned photoconductor layer comprises a frame portion extending around a periphery of the bottom electrode, the light-independent dielectrophoresis trap feature extending within said frame portion, the at least one raised region further comprising a circulation path joining the light-independent dielectrophoresis trap feature to the frame portion, and the scanning of the ring-shaped light pattern follows a trajectory from the frame portion to the light-independent dielectrophoresis trap feature through said circulation path.

13. The method according to claim 9, wherein the step of moving the particle of interest comprises projecting a ring-shaped light pattern onto the patterned photoconductor layer, a central area of said ring shaped light pattern defining the OET light trap.

14. The method according to claim 10, wherein the moving of the particle of interest further comprises scanning the ring-shaped light pattern over the raised regions of the patterned photoconductor layer.

15. An optoelectronic tweezers array, comprising a plurality of patterned optoelectronic tweezers (p-OET) device, each p-OET device comprising:
a top and a bottom electrode arranged in a parallel spaced apart relationship and forming a chamber therebetween; and
a patterned photoconductor layer provided on the bottom electrode inwardly of said chamber, the patterned photoconductor layer forming a pattern comprising at least one raised region where the bottom electrode is coated by a photoconductor material and at least one hollow region where the bottom electrode is exposed, the pattern comprising one or more boundaries between the raised and hollow regions, said boundaries defining a light-independent di electrophoresis trap feature.

16. A method for trapping a particle of interest, comprising the steps of:
a. providing a p-OET device having a patterned photoconductor layer forming a pattern comprising at least one raised region and at least one hollow region, the pattern comprising one or more boundaries between the raised and hollow regions, said boundaries defining a light-independent dielectrophoresis trap feature;
b. using an OET light pattern, moving the particle of interest in the light-independent dielectrophoresis trap feature of the p-OET device; and
c. stopping operation of the OET light pattern;
whereby the particle of interest remains in the light-independent dielectrophoresis trap feature after said stopping operation of the OET light pattern.

17. A patterned optoelectronic tweezers (p-OET) device, comprising:
a top and a bottom electrode arranged in a parallel spaced apart relationship and forming a chamber therebetween; and
a patterned photoconductor layer provided on the bottom electrode inwardly of said chamber, the patterned photoconductor layer forming a pattern comprising at least one raised region where the bottom electrode is coated by a photoconductor material and at least one hollow region where the bottom electrode is exposed, the pattern comprising one or more boundaries between the raised and hollow regions, the at least one raised region comprising a frame portion extending around a periphery of the bottom electrode, a trap portion extending within said frame portion and a circulation path joining the frame portion and the trap portion.

18. The p-OET device according to claim 17, wherein each of the top electrode and bottom electrodes comprises a substrate coated with a conductive layer on a side thereof facing the other one of said top and bottom electrodes.

19. The p-OET device according to claim 18, wherein the conductive layer of each electrode is made of indium tin oxide or a metallic material.

20. The p-OET device according to claim 17, wherein the photoconductor material is hydrogenated amorphous silicon or Titanyl phthalocyanine.

21. The p-OET device according to claim 17, wherein the boundaries of the patterned photoconductive layer define a permanent trap feature.

22. The p-OET device according to claim 17, in combination with a voltage source connected to the top and bottom electrodes.

23. Use of a p-OET device according to claim 17, in combination with and OET micromanipulation system to trap at least one particle.

24. A method for trapping a particle of interest, comprising the steps of:
a. providing a patterned optoelectronic tweezers (p-OET) device comprising a top and a bottom electrode arranged in a parallel spaced apart relationship and forming a chamber therebetween, and further comprising a patterned photoconductor layer provided on the bottom electrode inwardly of said chamber, the patterned photoconductor layer forming a pattern comprising at least one raised region where the bottom electrode is coated by a photoconductor material and at least one hollow region where the bottom electrode is exposed, the pattern comprising one or more boundaries between the raised and hollow regions defining a permanent trap feature, wherein the at least one raised region of the patterned photoconductor layer comprises a frame portion extending around a periphery of the bottom electrode, a trap portion extending within said frame portion and a circulation path joining the frame portion and the trap portion, and the scanning of the ring-shaped light pattern follows a trajectory from the frame portion to the trap portion through said circulation path;
b. introducing a solution containing the particle of interest in the chamber of the p-OET device;
c. using an OET light trap, moving the particle of interest in the permanent trap feature of the p-OET device; and
d. stopping operation of the OET light trap.

* * * * *

UNITED STATES PATENT AND TRADEMARK OFFICE
CERTIFICATE OF CORRECTION

PATENT NO. : 10,953,408 B2
APPLICATION NO. : 16/560549
DATED : March 23, 2021
INVENTOR(S) : Wheeler et al.

Page 1 of 1

It is certified that error appears in the above-identified patent and that said Letters Patent is hereby corrected as shown below:

On the Title Page

Item [73]:
Please correct "THE GOVERNING COUNCIL OF THE UNIVERSITY OF TORONTO BANTING INSTITUTE"
To read -- THE GOVERNING COUNCIL OF THE UNIVERSITY OF TORONTO --

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*